United States Patent [19]

Wright

[11] 4,225,717
[45] Sep. 30, 1980

[54] 2-HYDRAZINO-3-PYRIDINOL-1-OXIDE HYDROBROMIDE

[75] Inventor: George C. Wright, Norwich, N.Y.

[73] Assignee: Morton-Norwich Products, Inc., Norwich, N.Y.

[21] Appl. No.: 56,025

[22] Filed: Jul. 9, 1979

[51] Int. Cl.$^2$ .......................................... C07D 211/94
[52] U.S. Cl. ................................................. 546/306
[58] Field of Search ....................................... 546/306

[56] References Cited
U.S. PATENT DOCUMENTS 4,151,162  4/1979  Lang et al. ........................... 546/306

*Primary Examiner*—John M. Ford
*Attorney, Agent, or Firm*—Anthony J. Franze

[57] ABSTRACT

2-Hydrazino-3-pyridinol-1-oxide hydrobromide is a useful antibacterial agent.

1 Claim, No Drawings

2-HYDRAZINO-3-PYRIDINOL-1-OXIDE HYDROBROMIDE

This invention is concerned with the chemical compound 2-hydrazino-3-pyridinol-1-oxide hydrobromide. It is a useful antibacterial agent particularly in the therapy of urinary tract infection due to its appearance in the urine of the host to whom it is administered. Thus when administered perorally and intraperitoneally simultaneously to rats in a dose of 50 mg/kg by each route in a vehicle of 1% sodium carboxymethylcellulose, the urine from said rats possesses antibacterial activity in respect of *Escherichia coli* and *Staphylococcus aureus,* both of which are well-known urinary tract pathogens.

The compound of this invention can be formulated in a variety of dosage forms such as tablets, elixirs, suspensions and capsules to provide readily administrable compositions.

The method currently preferred for the compound of this invention is described in the following example:

To a mixture of m-chloroperbenzoic acid (18 g, 0.10 mole) and $CHCl_3$ (110 ml) was added 2-bromo-3-pyridinol (15 g, 0.086 mole) with mechanical stirring. The reaction mixture was stirred at room temperature overnight, cooled slightly using an ice bath and filtered. The solid was washed with 30 ml of cold $CHCl_3$ and ether (180 ml), and air dried, m.p. 186°–188°. Yield: 16 g. (100%).

To a mixture of the above described 2-bromo-3-pyridinol-1-oxide (13.4 g, 0.071 mole) in methanol (137 ml), was added $N_2H_4.H_2O$ (13.7 ml, 0.28 mole) over 0.1 hour with a temperature rise to 35°. The slurry was refluxed for 2 hours and filtered. The filtrate was concentrated under reduced pressure to give a tacky residue. The residue was slurried with 80 ml of isopropanol, refrigerated 3 days and filtered. The solid was washed with a portion of the filtrate and air dried to a constant weight, m.p. 158°–160°. Yield: 12 g (75%).

The analytical sample (m.p. 160°–161°) was obtained by drying a portion of the initial product for 18 hours at room temperature in vacuo over KOH.

Anal. Calcd. for $C_5H_7N_3O_2.HBr$: C, 27.04; H, 3.63; N, 18.93. Found: C, 26.01; H, 3.69; N, 18.73.

What is claimed is:

1. The compound 2-hydrazino-3-pyridinol-1-oxide hydrobromide.

* * * * *